(12) United States Patent
Favero (10) Patent No.: US 9,714,889 B2
(45) Date of Patent: Jul. 25, 2017

(54) SAMPLING PROCEDURE FOR POLYMER-BASED SOLUTIONS USED IN UNDERGROUND FORMATIONS

(75) Inventor: Cedrick Favero, Saint-Romain-le-Puy (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 507 days.

(21) Appl. No.: 14/130,015

(22) PCT Filed: Jul. 2, 2012

(86) PCT No.: PCT/EP2012/062805
§ 371 (c)(1),
(2), (4) Date: Dec. 30, 2013

(87) PCT Pub. No.: WO2013/004650
PCT Pub. Date: Jan. 10, 2013

(65) Prior Publication Data
US 2014/0134749 A1 May 15, 2014

(30) Foreign Application Priority Data
Jul. 4, 2011 (FR) ..................................... 11 56024

(51) Int. Cl.
*G01N 1/34* (2006.01)
*C09K 8/588* (2006.01)
(Continued)

(52) U.S. Cl.
CPC ............... *G01N 1/34* (2013.01); *C09K 8/588* (2013.01); *C09K 8/882* (2013.01); *G01N 1/2035* (2013.01);
(Continued)

(58) Field of Classification Search
CPC ........................................................ G01N 1/34
(Continued)

(56) References Cited

U.S. PATENT DOCUMENTS 3,234,163 A 2/1966 Schurz et al.
3,235,523 A 2/1966 Schurz et al.
(Continued)

FOREIGN PATENT DOCUMENTS

EP 2078947 7/2009
EP 2283915 2/2011
(Continued)

OTHER PUBLICATIONS

English Translation of specification of FR2935488 obtained from Espacenet on May 12, 2016.*
(Continued)

*Primary Examiner* — Christine T Mui
*Assistant Examiner* — Emily Berkeley
(74) *Attorney, Agent, or Firm* — Clark & Brody (57) ABSTRACT

This invention concerns a sampling procedure for an aqueous hydrosoluble polymer solution flowing in a main circuit, enabling a sample to be collected to undergo at least one analysis under ambient air giving at least one property of the hydrosoluble polymer characterised in that a stabilizing solution is added to the aqueous hydrosoluble polymer solution, according to a discontinuous addition method, before or after sampling from the main circuit, so as to obtain a sample comprising a mixture of aqueous hydrosoluble polymer solution and stabilizing solution in which the hydrosoluble polymer is protected against attacks it may undergo in an atmosphere containing at least 10% by volume of oxygen.

10 Claims, 4 Drawing Sheets

(51) Int. Cl.
*C09K 8/88* (2006.01)
*G01N 1/20* (2006.01)
*G01N 33/28* (2006.01)

(52) U.S. Cl.
CPC ..... *G01N 33/2823* (2013.01); *Y10T 436/2525* (2015.01)

(58) Field of Classification Search
USPC .......................................................... 436/176
See application file for complete search history.

(56) References Cited

U.S. PATENT DOCUMENTS

| | | | |
|---|---|---|---|
| 3,343,601 | A | 9/1967 | Pye |
| 4,141,842 | A | 2/1979 | Abdo |
| 4,317,759 | A | 3/1982 | Kanda et al. |
| 4,481,316 | A | 11/1984 | Kanda et al. |
| 4,622,356 | A | 11/1986 | Jarovitzky et al. |
| 4,795,575 | A | 1/1989 | Southwick et al. |
| 4,925,578 | A | 5/1990 | Southwick et al. |
| 5,296,577 | A | 3/1994 | Tamura et al. |
| 6,007,235 | A * | 12/1999 | Freud ................... G01N 1/2035 366/136 |
| 2005/0279499 | A1 | 12/2005 | Tarvin et al. |

FOREIGN PATENT DOCUMENTS

| | | | |
|---|---|---|---|
| FR | 2604444 | 4/1988 | |
| FR | 2935488 | 3/2010 | |
| FR | 2935488 A1 * | 3/2010 | ........... G01N 1/2035 |
| FR | WO 2010133258 A1 * | 11/2010 | ............. C08K 5/005 |
| JP | 57-159839 | 10/1982 | |
| WO | 99/00656 | 1/1999 | |
| WO | 99/44033 | 9/1999 | |
| WO | 2010/133258 | 11/2010 | |

OTHER PUBLICATIONS

S. Thomas, "Enhanced Oil Recovery—An Overview", Oil & Gas science and technology—IFP Review, vol. 63, No. 1, pp. 9-19 (2008).

* cited by examiner

SAMPLING PROCEDURE FOR POLYMER-BASED SOLUTIONS USED IN UNDERGROUND FORMATIONS

This invention concerns the technical field of polymer-based solution(s) used in underground formations, and particularly in enhanced oil recovery. More precisely, the subject of this invention is a process enabling a sample of an aqueous solution containing a hydrosoluble polymer to be collected directly from the circulating line of the said aqueous solution and allowing maintaining the integrity of the solution. The invention also concerns a device appropriate to implement the sampling procedure of the invention.

Most currently-exploited oil formations are matured. As a result a decline in their oil production is observed or is on the point of doing so. The recovery rate for these fields is now ever limited and is of the order of 15 to 35% on average. They therefore still offer considerable production potential.

The recovery of oil contained in oil fields is generally performed in several steps. Production results firstly from the natural energy of the fluids and the rock as they decompress. After this depletion phase, the quantity of hydrocarbons recovered to the surface represents an average of some 5 to 15% of the initial reserve. As a second step it is therefore necessary to use techniques aimed at increasing the recovery yield by maintaining pressure in the field.

The method often used consists of injecting water into the oil formation, through injector wells drilled for the purpose. This technique is called secondary recovery. This second phase is stopped when the water content is too high in the blend produced through the producer wells. The gain by this method in terms of additional recovery rate is about 10 to 20%.

Other techniques used are grouped under the name enhanced oil recovery (EOR). Their aim is to recover between 10 and 45% additional hydrocarbons. Various techniques are known under the term enhanced oil recovery, such as so-called thermal techniques, based on miscible fluids, and chemical techniques for enhanced recovery of oil remaining place (cf. Oil & gas science and technology—IFP review, vol 63 (2008) no.1, pp 9-19). By oil must be understood any type of hydrocarbon (which may also be called oil in the description that follows), namely light hydrocarbons as well as heavy and even bituminous hydrocarbons.

In chemical techniques, the efficiency of sweeping by water injection is generally improved by adding hydrosoluble polymers. The expected and proven benefits of using hydrosoluble polymers—through "viscosification" of injected waters—are improved sweeping and control of mobility in the field, in order to recover the oil rapidly and efficiently. Experts know that synthetic hydrosoluble polymers and in particular those based on acrylamide are very beneficial polymers for increasing the viscosity of aqueous solutions and are thus most frequently used for enhanced oil recovery.

In addition to the hydrosoluble polymer used and intended to increase viscosity of the solution, the injected aqueous solution can contain other chemical compounds to aid enhanced oil recovery. Among these other chemical compounds, there are weak, strong or very strong bases, mineral or organic bases. These bases saponify crudes and produce in situ surface-active species that solubilise oil. Examples of such bases are sodium carbonate and caustic soda, borate and metaborate compounds, amines, basic polymeric species . . . . Another family of compounds widely injected with polymers is surface-active compounds called surfactants, frequently anionic, zwitterionic, cationic and sometimes also non-ionic. These compounds are rarely injected pure, but with a co-surfactant and a co-solvent to improve compatibility and effectiveness in the reserve.

One of the problems encountered when using these aqueous solutions based on hydrosoluble polymers is that the polymers can be subject to chemical degradation. Such chemical degradation is due firstly to the formation of free radicals that react with the main polymer chain and result in a decrease of molar mass. These results in a fall in viscosity of the solution associated with a reduced hydrodynamic volume. Free radicals can arise from different sources: they may be generated by splitting of weak bonds in the polymer chain under the influence of heat/friction or by initiator residues or by-product impurities. Red/ox systems also generate free radicals. The presence of oxygen is the most damaging factor affecting polymer degradation. In addition, the polymer degradation reaction involving oxygen is amplified by the presence of metal such as iron or by the presence of hydrogen sulphide. Such degradation can therefore occur in the pipe in which the hydrosoluble polymer solution is flowing, in wells, but also when taking samples, especially if the samples are exposed to the open air since the polymer will be exposed to oxygen level higher than in pipes or in the well.

Furthermore, in addition to chemical degradation, the polymer can be subject to biological degradation in the reservoir (bacteria, etc.) and mechanical degradation (when injected into the well). Its concentration in solution can be reduced due to adsorption onto the reservoir rock and due to the dilution effect from aquifer. It is important to be able quantify the impact of each type of degradation on the polymer, in order to optimize the condition of injection of the aqueous polymer solution. However, when taking samples of the aqueous polymer solution, there is very often contact with oxygen from air, whether desired or not, resulting in rapid degradation of the polymer, making it unsuitable for the analyses, or providing misleading information.

In this context, it is important to be able to check precisely the quality of the injected aqueous hydrosoluble polymer solution at different stages of polymer enhanced oil recovery process, for example before or after introduction into reservoirs oil, in order to predict or assess performance of the injection within the well. To properly do so, it is necessary to have sampling techniques allowing maintaining integrity of the polymer, something that is not without difficulty.

The applicant has developed a chemical formulation including a combination of stabilizing additives and a polymer in powdered form that is particularly useful for enhanced oil recovery. Such a formulation is described in patent application WO 2010/133258. Using this formulation inhibits the different types of chemical polymer degradation that occur in the well. Nonetheless, using this formulation in which stabilizing agents are introduced continuously has a certain cost and requires handling large quantities of sometimes hazardous chemicals. The quantities of stabilizing formulation to be used are therefore minimized to protect against the likely risk of degradation in the well where, generally, low levels of oxygen are present at about 0.1 ppm. The stabilizing formulation considered in this context is not therefore able to stabilise the polymer when taking samples to the open air (containing about 6 ppm oxygen) with the contamination levels generally observed, which most frequently consist of iron derivatives or $H_2S$.

Ideally samples should be analysed under an inert atmosphere by using a glove box, for example, which itself poses logistical problems when considering offshore platforms operations in particular.

Many companies have also developed in-line viscometers for determining the viscosity of aqueous polymer solution. However, the aqueous polymer solutions used are non-Newtonian fluids with pseudo-plastic properties. As a result, their viscosity depends on the shear rate applied on the solution during measurement. Currently available in-line measurement techniques do not allow correcting for the shear rate applied to the fluid, making the resulting viscosity measurement in accurate.

Due to the difficulty associated with analysing the aqueous solution before it enters the well, experts have developed techniques to collect samples of the aqueous solution inside the well itself. In patent US2005/0279499 held by Schlumberger, an auxiliary well is drilled, into which a probe is introduced. However, these techniques are very cumbersome and expensive to use.

It therefore appears that current sampling methods to collect, on the fluid circuit, an aqueous polymer solution, as in enhanced hydrocarbon recovery or hydraulic fracturing, do not enable a stable and representative sample to be collected from the circulating solution in particular in difficult field conditions.

This invention is intended to overcome the problems described above.

In this context, the invention offers a sampling procedure for an aqueous hydrosoluble polymer solution flowing in a main circuit, enabling a sample to be collected to undergo at least one analysis under ambient air giving at least one property of the hydrosoluble polymer characterised in that a stabilizing solution is added to the aqueous hydrosoluble polymer solution, according to a discontinuous addition method, before or after sampling from the main circuit, so as to obtain a sample comprising a mixture of aqueous hydrosoluble polymer solution and stabilizing solution in which the hydrosoluble polymer is protected against attacks it may undergo in an atmosphere containing at least 10% by volume of oxygen.

'Protected against attacks it may undergo' means that the integrity of the polymer is maintained due to the choice of composition and volume of stabilizing solution introduced, i.e. that the main types of degradation due to the simultaneous presence of oxygen and contaminants, such as $H_2S$, iron derivatives or other oxidation-reduction systems are avoided for a period of at least 1 hour, preferably at least 1 day, preferably at least 7 days and preferentially for at least 30 days. It may be considered that during this period, at least 90% of the degradation that the polymer would undergo in the same solution and under the same conditions, but in the absence of introducing the stabilizing solution, is avoided. According to one specific embodiment, the nature and volume of the stabilizing solution introduced are chosen so as to obtain a sample in the form of a mixture of the aqueous hydrosoluble polymer solution and stabilizing solution in which the hydrosoluble polymer is protected against attacks it may undergo in an atmosphere containing from 17% to 22% oxygen by volume, so in particular ambient air.

In particular, the added stabilizing solution enables the measured viscosity of the sample to be maintained constant, when it is measured in ambient air, for a period of at least 1 hour, preferably at least 1 day, preferably at least 7 days and preferentially for at least 30 days. It can be considered that ambient air is an atmosphere containing from 17% to 22% oxygen by volume. 'Main circuit' means the assembly that comprises pipe but may also include storage or maturation vessels, in which the polymeric solution flows. Samples may be collected from pipes or from storage or maturation vessels where the flow of polymer is naturally much slower.

According to specific embodiments, the procedure according to the invention includes one of the following characteristics or any combination of these characteristics:
- the procedure according to the invention includes a step to determine the volume of stabilizing solution to be added to the aqueous hydrosoluble polymer solution in which the volume of stabilizing solution added is varied and the change in measured viscosity of the blend obtained is studied over time, after exposure to air,
- the procedure according to the invention includes a characterisation step under ambient air of the sample comprising a blend of the aqueous hydrosoluble polymer solution and the stabilizing solution; such a step may in particular correspond to measuring the viscosity of the hydrosoluble polymer in the sample,
- the volume of stabilizing solution in the blend is less than 25%, and is preferably between 1 and 10% of the total sample volume; in particular such a choice means the viscosity measurement is not influenced by dilution effect and/or the solubilizing properties of the aqueous phase, is not modified,
- the aqueous hydrosoluble polymer solution circulates in a main circuit used in enhanced oil recovery, either on the injection side or on the production side and the sample is collected downstream and/or upstream of the oil reservoir,
- the procedure according to the invention includes a sampling step of a volume of aqueous hydrosoluble polymer solution in a sampling tank by using a sampling pipe fitted with a non-shearing sampling closure and a step involving adding a volume of stabilizing solution to the sampling tank, the sampling and addition steps being carried out under hermetically-sealed conditions,
- the procedure according to the invention uses a sampling device connected to the main circuit in which the aqueous hydrosoluble polymer solution to be sampled is flowing, including:
  - a first vessel, called the sampling tank, intended to contain the sampled fluid, including:
    - an inlet for aqueous polymer solution to be sampled, and a sampling pipe connecting this inlet to the main circuit, the said sampling pipe being fitted with a non-shearing sampling closure and being intended to be connected to the main circuit and
    - an outlet and outlet pipe fitted with an outlet closure and connected to the outlet,
  - a second vessel, called the treatment tank, intended to contain a stabilizing solution, comprising an outlet for the stabilizing solution and a connecting pipe connected to the outlet for the stabilizing solution and fitted with a closure treatment and providing, at least in part, the connection between the treatment tank and the sampling tank,
- and where the sampling tank is connected hermetically to the main pipe, and is isolated hermetically when the sampling closure, outlet closure and treatment closure, as well as any other closures that may be present to provide communication from the sampling tank to the outside, are closed.

The procedure according to the invention enables in-line sampling of an aqueous polymer solution while maintaining sample integrity, and in particular limiting the main types of degradation of the polymer due to contact of the solution with oxygen in the presence of iron and/or hydrogen sulphide, when taking the sample and/or later when analysing the sample.

According to another of its aspects, independent of the previous one, the purpose of the invention is also a sampling procedure for an aqueous hydrosoluble polymer solution circulating in a main circuit, enabling a sample to be collected to undergo at least one analysis under ambient air, which includes a sampling step for a volume of aqueous hydrosoluble polymer solution in a sampling tank using a sampling pipe fitted with a non-shearing closure and a step of adding to the sampling tank a volume of a stabilizing solution, the sampling and addition steps being carried out under hermetically-sealed conditions.

According to another of its aspects, the purpose of this invention is also a sampling device for collecting a sample from an aqueous polymer solution, intended to be connected to a main circuit in which the aqueous polymer solution is circulating, characterised in that it comprises:

a first vessel, called the sampling tank, intended to contain the sampled fluid, including:
  an inlet for aqueous polymer solution to be sampled, and a sampling pipe connected to this inlet, the said sampling pipe being fitted with a non-shearing sampling closure and being intended to be connected to the main circuit and
  an outlet and outlet pipe an outlet closure and connected to the outlet,
a second vessel, called the treatment tank, intended to contain a stabilizing solution, comprising an outlet for the stabilizing solution, a connecting pipe connected to the outlet for the stabilizing solution and fitted with a treatment closure and providing, at least in part, the connection between the treatment tank and the sampling tank,
and where the sampling tank is isolated hermetically when the sampling closure, outlet closure and treatment closure, as well as any other closures that may be present to provide communication from the sampling tank to the outside, are closed.

According to a specific embodiment, the device is connected to the main circuit by a sampling pipe, the sampling tank and the main circuit being hermetically connected.

According to a specific embodiment that may be combined with the previous one, the non-shearing sampling closure is a ball valve.

As part of this invention, the stabilizing solution contains at least one stabilizing agent chosen from deoxygenating agents, precipitating agents, free radical scavengers, complexing agents, H$_2$S-absorbing agents and sacrificial agents. Preferably, the stabilizing solution contains at least three stabilizing agents chosen from deoxygenating agents, precipitating agents, free radical scavengers, complexing agents, H$_2$S-absorbing agents and sacrificial agents.

From such stabilizing agents, well known to experts, will conventionally be selected depending on the conditions encountered when using the polymer, as those presented in Table 1 below.

TABLE 1

| Conditions for using the polymer | | Stabilizer | Role of the stabiliser |
|---|---|---|---|
| Restrict free-radical degradation of the polymer by: | action on sources causing or accelerating free radical formation | deoxygenating agent precipitating agent | Eliminate residual oxygen Complex and precipitate metallic ions to reduce their activity |
| | | H$_2$S absorbing agent | Capture H$_2$S present |
| | action to capture free radicals formed before they attack the polymer | Free radical scavenger | Form more stable radicals causing less degradation to the polymer chain |
| | | sacrificial agent | React very rapidly with radicals formed to absorb them |
| Restrict thermal degradation of the polymer | by complexing action on ions having the ability to interact with anionic groups of the polymer and so reduce its viscosity or even precipitate it | complexing agent | Complex metallic ions with valency of two or more, in the wider sense (transition metals, alkalines, alkaline earths) |

The following stabilizing agents are given as examples from among those most commonly described in the literature:

as deoxygenating agents:

Commonly-described deoxygenating agents are compounds such as sulphite, bisulphite, metabisulphite, dithionite, hydrazine and its hydroxylamine derivatives. Their use for polyacrylamides is described in U.S. Pat. No. 3,343,601. All act as reducing agents modifying the redox potential of the aqueous formulation. In this class of chemical compounds we can also consider organic sulphites such as alkyl sulphites, alkyl hydrosulphites, suiphinates, sulphoxylates and phosphites, but also oxalic or formic acid, erythorbate salts and carbohydrazides. These compounds enable traces of oxygen in injection water to be eliminated, typically achieving dissolved oxygen levels below 200 ppb (parts per billion). For preference, in keeping with physico-chemical, toxicological and industrial criteria, organic and inorganic sulphite-type deoxygenating compounds are particularly advantageous. For example we will mention Na$_2$SO$_3$ (sodium sulphite) and NaDT (sodium dithionite, Na$_2$S$_2$O$_4$).

as precipitating agents:

Commonly-described precipitating agents reacting with metals used in redox reactions are generally anionic compounds. In fact, their mode of action is to form a poorly-soluble complex with metal cations in solution. These are hydroxides, carboxylates, carbonates, arsenates, cyanurates, phosphorated salts and sulphurated salts. In the case of iron, a metal often present in production water used to prepare polymer solutions, we will list as compounds from the phosphated salts family sodium phosphate, sodium hydrogen phosphate and phytic acid; and for compounds from the sulphurated salts family, sodium sulphide and sodium hydrosulphide; and for the carbonate family, sodium carbonate. In addition to their efficacy, sodium carbonate and sodium phosphate are preferentially used due to their low cost, availability, low toxicity and physico-chemical properties.

as H$_2$S absorbing agent: triazine derivatives, chlorites, sodium hypochlorite, ternary amines and aldehydes such as glyoxal.

as free radical capture agents:

Free radical scavengers are most frequently sulphated compounds, stearically-hindered amines, aromatic compounds or nitroxides. These compounds can react with radicals to form a stable species in which the radical finds itself trapped. The radical is then no longer available to degrade the polymer. There are numerous compound developed to capture radicals and stabilize polymers. We can list the following compounds as examples: thiourea, 2-mercaptobenzothiazole, dimedone, N,N'-dimethylthiourea, N,N'-diethylthiourea N,N'-diphenylthiourea, ammonium thiocyanate, tetramethylthiuram disulfide, 2,2'-dithiobis (benzothiazole), sodium dimethyldithiocarbamate, propyl parametoxyphenol, 3,4,5-trihydroxybenzoate, 2,6-di-tert-butyl-4-methylphenol, 2,5-Di(tert-amyl)hydroquinone, 4,4'-thiobis(6-tert-butyl-m-cresol), ammonium N-nitrosophenylhydroxylamine, butylhydroxyanaisole, hydroxy-8-quinoleine, 4-hydroxy-2,2,6,6-tetramethyl-piperidinooxy (HTPO), 5-hydroxy-1,4-naphtoquinone, (N-(1,3-dimethylbutyl) N'-phenyl-p-phenylenediamine, 2,6-di-tert-butyl-4-methylphenol, 2,5-Di(tert-amyl)hydroquinone, 4,4'-thiobis (6-tert-butyl-m-cresol), dicyandiamide, guanidine, cyanamide, etc.

This list cannot be exhaustive due to the number of possible variations that can be made with these compounds from frequently complex chemistries. For preference the following are used: thioureas and alkylthioureas, mercaptobenzoimidazole (MBI), mercaptobenzothiazole (MBT) and their combinations as used by Shell, Diafloc and Nitto (U.S. Pat. Nos. 4,317,759, 4,925,578, 4,481,316, 4,795,575, 5,296,577), thiourea (U.S. Pat. No. 3,235,523), butyl hydroxyanisole, paramethoxy phenol, quinolinol as mentioned in patent application JP57-159839 by Mitsubishi Chemicals, 5,5 dimethyl-1,3-cyclohexane dione used in U.S. Pat. No. 4,622,356 by American Cyanamid, or sodium thiocyanate used in U.S. Pat. No. 3,234,163 by Dow Chemical. In addition to performance, taking into account of the physico-chemical, toxicological and economic properties, it is advantageous to use diethyl thiourea, dimethyl thiourea, mercaptobenzothiazole or mercaptobenzoimidazole, without being limited to these.

as sacrificial agents:

Sacrificial agents are most frequently from the alcohol family as described in U.S. Pat. No. 4,141,842 or in patent application JP 57-159839. The use of hydrosoluble monomers has also been described in patent application FR 2604444. The alcohol, by virtue of its hydroxl functional group, is oxidised to its ketone form and so consumes the radical, while the monomer, with its double bond, consumes the radical by radical polymerisation. Due to the large number of chemicals falling under these description, it is impossible to list all the alcohols and monomers that can be used. Most of the monomers making up hydrosoluble polymers are suitable and as the monomers of choice we can mention, without any restrictions, diallyl dimethyl ammonium chloride, acrylamide and methacrylamide.

Alcohols can be mono-alcohols or polyols and one selection criterion is the number of hydroxyl groups per unit mass and their solubility in water. Of particular interest, and again without any restrictions, we can list glycerol, propylene glycol, trimethyleneglycol, isopropanol, 1,2-butanediol, 1,3-butanediol, 1,4-butanediol, 2,3-butanediol, 1,2,4-butanetriol, pentaerythritol (PETA), trimethylolethane, neopentylglycol, 1,2-pentanediol, 2,4-pentanediol, 2,3-pentanediol, trimethylolpropane, 1,5-pentanediol and partially or totally hydrolysed polyvinyl alcohol.

as complexing agents:

Commonly-described complexing agents reacting with metals present in brines are generally anionic compounds. In fact, their mode of action is to form a highly-soluble complex with high affinity for metal cations in solution. Such complexing agents may be carboxylate derivatives, phosphated derivatives, amino acids, sulphonates, etc. These agents can be present in the form of small molecules or polymers. As examples of polymers, we can list polyacrylates from the polymerisation of acrylic acid, copolymers with sulphonated groups (from ATBS, vinyl sulphonic acid, allyl sulphonic acid, methallyl sulphonic acid, etc.) or maleates (from maleic anhydride), and terpolymers including a non-ionic monomer such as acrylamide, styrene, hydroxypropyl acrylate, etc. We can also list polyacetates, polycarboxylates, polyaspartates, polyphosphates, polyphosphonates and polysuccinates.

For small molecules, we can list ascorbic acid (tetrasodium iminodisuccinate), citric acid, dicarboxymethylglutamic acid, ethylenediaminedisuccinic acid (EDDS), ethylenediamine-tetraacetic acid (EDTA), hepta sodium salt of diethylene triamine penta(methylene phosphonic acid) (DTPMP.Na$_7$), maleic acid, nitrilotriacetic acid (NTA), oxalic acid, polar amino acids, including arginine, asparagine, aspartic acid, glutamic acid, glutamine, lysine and ornithine, succinic acid, diethylenetriaminepentaacetic acid, disodium malonic acid, disodium tartaric acid, sodium tripolyphosphate, sodium hexametaphosphate, sodium silicate, iminodiacetic acid, 1,2 diaminopropane N tetraacetic acid, 1,2-cyclohexanediaminetetraacetic acid, N-(2-hydroxyethyl)ethylene diamine triacetic acid, diethylenetriaminepentaacetic acid, diethyl iminodiacetic acid, etc.

The stabilizing agent(s) present in the stabilizing solution will be selected preferentially:

for deoxygenating agents, sulphites in all forms, carbohydrazides and derivatives of hydrazine, or sodium erythorbate.

for precipitating agents, sodium carbonate and sodium phosphate

For H$_2$S absorbing agents, triazine derivatives, for free radical scavenger, dialkyl thiourea, HTPO, gallates, guanidine derivatives, mercaptobenzothiazole and mercaptobenzoimidazole for sacrificial agents, glycerol, propylene, glycol, trimethyleneglycol, isopropanol, 1,2-butanediol, 1,3-butanediol, 1,4-butanediol, 2,3-butanediol, 1,2,4-butanetriol, pentaerythritol (PETA), trimethylolethane, neopentylglycol, 1,2-pentanediol, 2,4-pentanediol, 2,3-pentanediol, trimethylolpropane, 1,5-pentanediol and partially or totally hydrolysed polyvinyl alcohol.

for complexing agents, polyacetates, polycarboxylates, polyaspartates, polyphosphates and polyphosphonates, polysuccinates, ethylene-diamine-tetraacetic acid (EDTA), the hepta sodium salt of diethylene triamine penta(methylene phosphonic acid) (DTPMP.Na$_7$), maleic acid, nitrilotriacetic acid (NTA), oxalic acid.

For preference, the stabilizing solution includes at least one deoxygenating agent, at least one free radical scavenger and at least one sacrificial agent, preferably chosen from those listed above.

The stabilizing solution preferably has a total concentration of stabilizing agents greater than 10%, ideally greater than 25%, these being percentages by weight expressed relative to the total mass of the stabilizing solution. If the stabilizing solution contains a solvent, this is ideally water.

The procedure according to the invention is of particular interest when samples will be subjected to later analysis, particularly to determine if the polymer present in the sample have been exposed to some degradation before sampling (change in molecular weight, concentration, viscosity, filterability or poor inversion of the emulsion), given that, according to the invention, the main degradation during sampling and later analysis can be avoided. Nonetheless, to protect the polymer against later degradation, it is important to add an appropriate quantity of stabilizing solution. This quantity can be determined empirically in advance, by taking different successive samples, each time adding a different quantity of stabilizing solution and comparing the measured viscosity of the solutions over time. This viscosity of successive samples can be, if possible, compared to an initial viscosity that this same polymer would generate before any degradation. The initial viscosity can be determined on a hydrosoluble polymer solution initially made in aqueous solution, i.e. before it has degraded, at the same concentration in the same aqueous solution, but by measuring the viscosity either in a glove box under an inert atmosphere, or in a laboratory study without any contaminant present.

For preference, viscosity measurements are made under non shear degrading conditions. The measured viscosity can be the Brookfield viscosity or measurement of the dynamic viscosity on a rheometer measured under non shear degrading conditions, for example measured as in the following examples. The right quantity of stabilizing solution to be added will be the volume enabling the measured viscosity to be maintained approximately constant over a period of at least 1 hour, preferably at least 1 day, preferably at least 7 days and preferentially for at least 30 days, from the moment when the sample comes into contact with ambient air, and therefore with oxygen. 'Approximately constant' means that the viscosity measured over this period changes by no more than 10%. According to a preferred embodiment, the volume of stabilizing solution introduced enables, over this period, the measured viscosity to be maintained constant without varying or varying by less than 5%.

Procedures and devices according to the invention are advantageous for sampling aqueous solutions of all types of hydrosoluble polymers, particularly these known to useful in oil recovery or hydraulic fracturing operations. Samples can be collected just before the aqueous polymer solution enters the oil well, before its injection into the rock. It will thus be possible to determine the quality of the polymer at the point of sampling and possibly provide, before injection, appropriate treatment with certain stabilizing additives, or adjusting the concentration or changing the injection parameters. It is also possible to use the device according to the invention on the production side of the oil reservoir, in order to determine if the polymer has been degraded during its propagation in the formation. Samples and checks can also be provided at the inlet and outlet to the oil reservoir or the rock.

In particular, the hydrosoluble polymer present in the aqueous solution to be sampled can, particularly, be any type of synthetic or natural organic polymers soluble in water. In particular, the hydrosoluble polymers described by the applicant in patent application FR 0953258 may be present in the injected aqueous solution. For example, we can mention the acrylamide-based polymers. Most frequently, the hydrosoluble polymer used has a molecular weight greater than or equal to 1 million g/mol, particularly belonging to the range from 1 to 35 million g/mol. We will favour acrylamide-based polymers, and particularly those in which the acrylamide represents, preferably, at least 10% by moles. In particular, the aqueous solution to be sampled can contain at least one acrylamide based copolymer selected from acrylic acid, 2-acrylamido-2-methylpropane sulphonic acid or N-vinyl pyrrolidone. It is possible that the aqueous solution sampled contains several hydrosoluble polymers.

The selection of monomers and different polymerisation additives, allows the polymer present in the aqueous solution sampled to be linear, branched or cross-linked structure, or to have a "comb polymer" or "star polymer" architecture.

Most frequently the aqueous polymer solution will be made in a brine solution. Optionally, the aqueous polymer solution may contain an alkaline agent, chosen for example from hydroxides, carbonates and bicarbonates of alkaline metal or ammonium, such as sodium carbonate. The aqueous polymer solution can also contain at least one surfactant.

The polymer concentration in the aqueous solution, and particularly in the brine, is generally greater than 50 ppm and most frequently between 100 and 30,000 ppm.

The detailed description below, by reference to the appended Figures, gives a better understanding of the invention.

Figure 1:
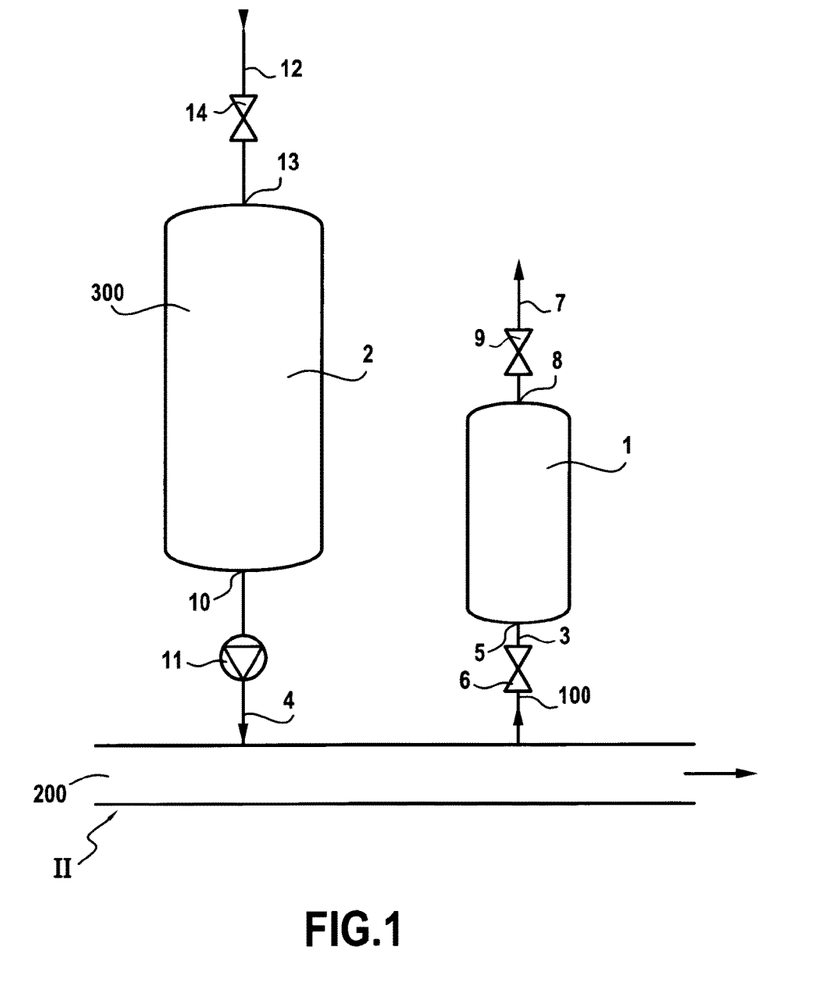
FIGS. 1 and 2 present drawings of different variants of implementation of the procedure according to the invention.

In the case illustrated in FIG. 1, stabilizing solution 300 is added directly into main circuit II in which the aqueous hydrosoluble polymer solution 200 to be sampled is circulating. In the embodiment illustrated, it is added to the previously-constituted aqueous solution, but it would also be possible to introduce it into the polymer dissolution water before its introduction, or even at the same time as introducing the polymer into the dissolution water, or with the addition of surfactants or other additives when these are present in the aqueous solution.

As illustrated in FIG. 1, a treatment tank 2 can be used to contain the stabilizing solution 300 and which includes an outlet 10 connected to the main circuit II by a treatment pipe 4 fitted with a treatment closure 11. Given the pressures generally existing in the main circuit, the treatment closure will frequently be a pump. In fact, the aqueous solution may be at high pressure inside the main circuit. In general, the pressure in the main circuit pipe is greater than 0.2 MPa (2 bars) and most frequently between 0.2 MPa and 80 MPa (2 and 800 bars).

The treatment tank 2 may take the form of an open-topped vessel for refilling or a closed vessel as illustrated in FIG. 1, in which case it is refilled using a refilling pipe 12 connected to an inlet 13 and fitted with a refilling closure 14.

Then, the sample comprising a mixture of stabilizing solution and the aqueous hydrosoluble polymer solution can be collected using a sampling tank 1 connected to the main circuit II, through a sampling pipe 3 connected to an inlet 5. This sampling pipe 3 is fitted with a non-shearing sampling closure 6 that, when open, allows the sample to pass through. The fact that this closure is non-shearing ensures that the sampled solution has not undergone mechanical degradation. As an example of a non-shearing closure that can be used as part of this invention, there are ball valves, progressive-cavitation or internal gear pumps. The sampling tank is also connected to an outlet pipe 7 at its outlet 8. This outlet pipe 7 is fitted with an outlet closure 9 that may be shearing or non-shearing. Such an outlet closure 9 must be non-shearing if the sample must subsequently be collected through it, to be submitted for characterisation. To fill the sampling tank 1, it is necessary for both the sampling closure 6 and outlet closure 9 to be open, given that the sampled fluid is incompressible. Before the sampling starts, the sampling tank 1 may contain liquid, air or, non-ideally, an inert gas like nitrogen or argon. When the sampling closure 6 and outlet closure 9 are opened, the aqueous polymer solution circulating under elevated pressure in the main circuit II will enter the sampling tank 1 by chasing the air or gas present in the sampling tank 1 through the outlet closure 8. So that the sample 100 that is going to be stored in the sampling tank does not come into contact with the air or inert gas present in the sampling tank 1, and in order to avoid contamination or degradation in the sampling tank, a flush is ideally performed first using the aqueous polymer solution 200 or a mixture of the aqueous polymer solution and stabilizing solution.

The stabilizing solution is added for the needs of sampling and is therefore performed in a discontinuous fashion. In other words, just before a sample is taken, a known quantity of stabilizing solution is added over a given time. This addition is adjusted, depending on the flow rate of the aqueous polymer solution circulating in the main circuit, so as to obtain the desired volume of stabilizing solution in the resulting mixture, and depending on the distance separating the addition point for the polymer solution and the sampling point, so ensuring that a sample contains a mixture of stabilizing solution and polymer solution. Between two samples collection, addition of stabilizing solution is stopped.

Figure 2:
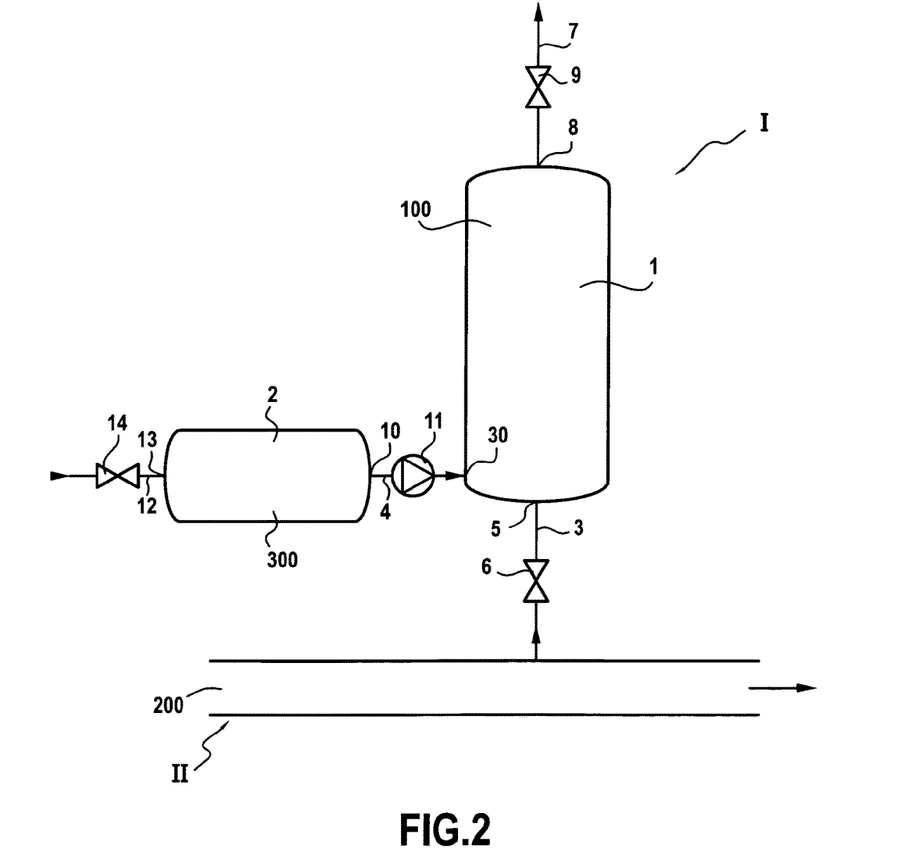

According to a preferred embodiment illustrated in FIG. 2, the procedure according to the invention uses a device enabling the stabilizing solution to be introduced into a sample of aqueous solution, and not directly into the main circuit, so enabling the consumption of stabilizing solution to be reduced. For the purposes of simplicity, the numbering used in FIG. 1 has been retained in FIG. 2 for the common items.

In FIG. 2, the treatment tank 2 is connected to the sampling tank 1. They are connected using a treatment pipe 4 directly linking the outlet 10 for stabilizing solution 300 located on the treatment tank 2 to an inlet 30 for the stabilizing solution 300 on the sampling tank 1. This treatment pipe 4 is fitted with a treatment closure 11, for example in the form of a high pressure pump, such as those used for liquid chromatography such as HPLC, which may be shearing or non-shearing. In devices according to the invention, closures may be valves or pumps, in particular. If the treatment closure 11 is a valve, the pressure in the treatment tank 2 will be greater than the pressure in the sampling tank 1. Conversely, when the treatment closure 11 is a pump, the pressures in the tanks may be independent, ie. identical or different.

For the rest, the two tanks and pipe used in the device presented in FIG. 2 are identical to those in FIG. 1. When the treatment closure 11 located on the treatment pipe 4 is open, the stabilizing solution can enter the sampling tank 1. The stabilizing solution may be added to the sampling tank 1 before or after, preferably after sampling from the aqueous hydrosoluble polymer solution. Flushing steps on the sampling tank will preferably be performed. The volumes introduced may be determined by any appropriate system, by determining the volumes coming out after outlet 8, or by using a flow rate measuring device in pipes 3 and/or 4.

Whatever the device variant I used, the sampling tank 1, connections, pipes and closures are selected so that the sampling tank 1 can be hermetically sealed from the outside and its connection to the main circuit II is achieved hermetically. In devices according to the invention, the sampling tank 1, and possibly the treatment tank 2, is hermetically sealed. In particular it may be gas bottles or cylinders. Preferably, the tanks and also the various pipes are made from austenitic stainless steel. Similarly, the various closures used will preferably be made from austenitic stainless steel.

In order to perform the analysis, the sample 100 located in the sampling tank 1 may be collected directly from the sampling tank 1, directly through the outlet 8, or through another outlet dedicated for the purpose, not shown. It is also possible that the sampling tank 1 may be separated from the rest of the equipment after each sample is collected, in which case the sample may be collected from the sampling tank 1 through the non-shearing inlet closure 6, the outlet closure 9 then being either shearing or non-shearing.

The various closures in devices according to the invention can be controlled either manually or automatically. In this case, a command unit will be provided enabling the various closures to be actuated.

The different advantages of this invention can be illustrated by the following examples, which are not limiting in nature.

Example 1

Sampling at Injection Under Off-Shore Conditions

A viscous polymer solution is prepared by dissolving an inverted emulsion containing a copolymer of 70 mol % acrylamide/30 mol % acrylic acid, partially neutralised using caustic soda. The average mass molecular weight of the copolymer is 18 million. The commercial name for such emulsion is Flopaam EM 533 EOR at SNF.

The water used comes from a water treatment unit in which traces of oxygen are eliminated by adding a 50 ppm ammonium bisulphite solution. The brine water used is composed as described below (Table 2) and contains about 10 ppm ferrous iron and 0 ppb $O_2$.

It is known that such water will not degrade the viscosity of the polymer solution, if and only if the solution remains completely free of oxygen. In fact, reintroducing any oxygen in the presence of iron and excess reducing agent will have an immediate effect by degrading the molecular weight of the polymer.

TABLE 2

| composition of brine for example 1 | |
|---|---|
| for 1,000 g | |
| NaCl | 15.4 g |
| $CaCl_2, 2H_2O$ | 2.54 g |
| $MgCl_2, 6H_2O$ | 2.1 g |
| $NaHCO_3$ | 0.62 g |

Figure 3:
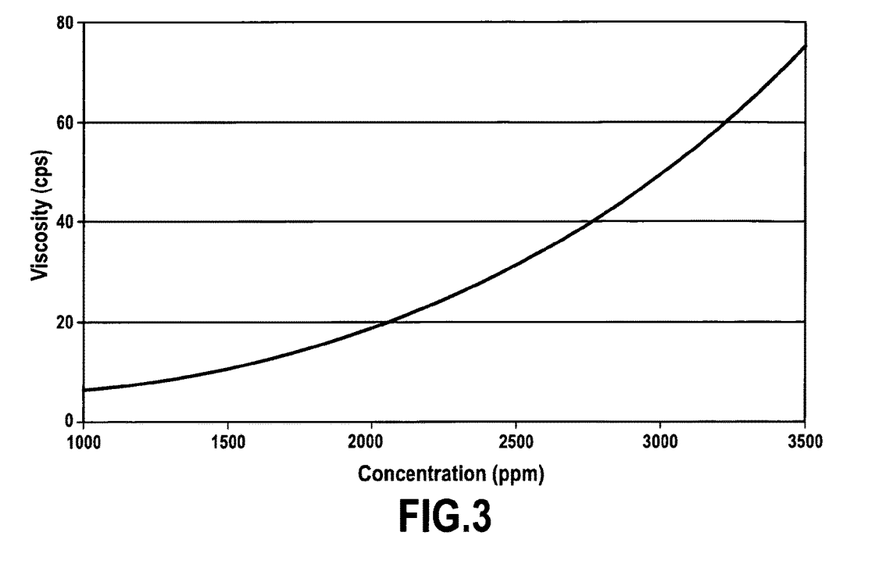
FIG. 3 shows the impact of concentration on the viscosity of a poly(acrylamide-co-acrylic acid) solution measured using a Brookfield viscometer, UL Spindle, 6 rpm, at 30° C.

In order to dissolve the polymer rapidly and avoid contamination with oxygen, the emulsion containing 30% active polymer is firstly inverted using a static mixer to obtain a 10,000 ppm polymer solution, then this solution is immediately diluted with the same brine water to obtain a polymer solution containing 3,000 ppm polymer, which according to the graph presented in FIG. 3 should generate a viscosity of 50 cps at 30° C., using a Brookfield viscometer with UL module at a speed of 6 rpm. Details of this procedure are described in EP2283915.

A sample is collected downstream of the polymer dissolution unit using a device comprising a sampling cylinder to which is connected a set of non-shearing valves, and a cylinder that may be used to inject a previously-prepared stabilizing solution. The construction of the device is represented schematically in FIG. 2.

The stabilizing solution is a mixture of 25% dimethyl thiourea, 25% HTPO (4-hydroxy-2,2,6,6-tetramethylpiperidin-1-oxyl) 25% glycerine and water, the percentages being % by weight given for the total weight of the stabilizing solution.

1-A A first sample is collected. The solution corresponding to the sample collected in the sampling cylinder is de-pressurised into a beaker under ambient air and after de-foaming, its viscosity is measured at 24° C. The loss of viscosity is immediate and the value measured in only 27 cps.

1-B A second sample is collected. The cylinder containing the sample collected is then disconnected from the rest of the device, transferred by helicopter to a measuring laboratory, and finally introduced into a glove box, an enclosure rendered inert by nitrogen purging so as to have less than 50 ppb of oxygen in the box. Therefore the measurement is made 2 days after collecting the sample. The viscosity is then 51 cps, which is the expected value. This value therefore confirms that the dissolution line remains strictly anaerobic and that no mechanical degradation occurred. This also confirms the quality of polymer dissolution and the accuracy of its concentration. However, it requires significant and slow measuring resources that do not enable real time or frequent checks of the quality of fluid injected.

1-C A third sample is collected. 100 ppm of stabilizing solution is then injected into the sampling cylinder using overpressure and is therefore added to the sample collected. After waiting 10 minutes mixing time, the cylinder is de-pressurised into a beaker under ambient air and after de-foaming the viscosity is measured at 24° C. The viscosity is 43 cps, equivalent to a degradation of about 14% compared to example 1-B, due to inadequate short stopping of the degrading reactions.

1-D A fourth sample is collected. 500 ppm of stabilizing solution is then added to the sample by injection into the sampling cylinder using overpressure. After waiting 10 minutes mixing time, the cylinder is de-pressurised into a beaker under ambient air and after de-foaming the viscosity is measured at 24° C. The viscosity is 51 cps and is therefore in perfect agreement with the expected value. This value therefore confirms that the dissolution line remains strictly anaerobic and that no mechanical degradation occurred. This also confirms the quality of polymer dissolution and the accuracy of its concentration. This technique requires minor and rapid measuring resources that enable real time and frequent checks of the quality of injected fluid.

1-E A fifth sample is collected. 1,000 ppm of stabilizing solution is then injected into the sampling cylinder using overpressure. After waiting 10 minutes mixing time, the cylinder is de-pressurised into a beaker under ambient air and after de-foaming the viscosity is measured at 24° C. The viscosity is 54 cps, a little above the expected value. This value is explained by overdosing the stabilizing solution, which modifies the viscosifying power of the polymer in this fluid.

Figure 4:
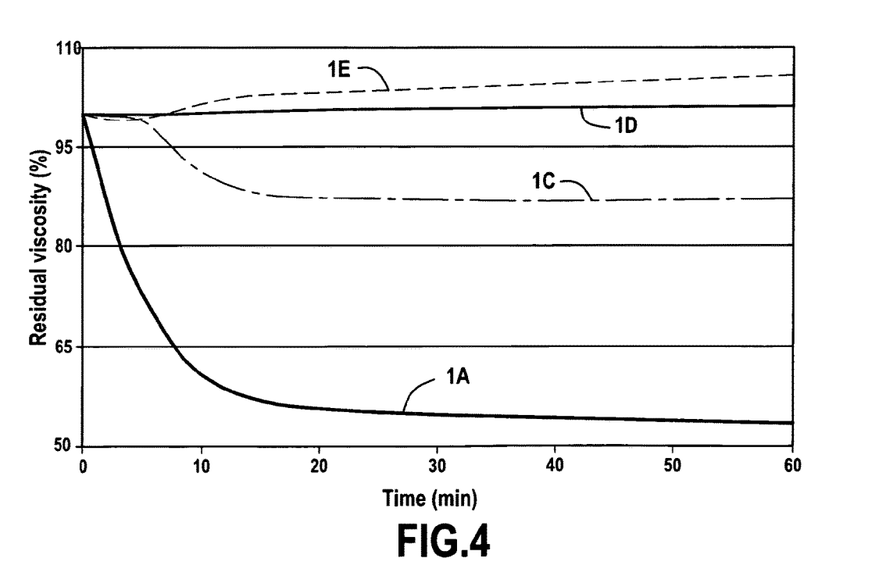
FIG. 4 shows the change in residual viscosity of a poly(acrylamide-co-acrylic acid) solution (viscosity being measured with a Brookfield viscometer, UL Spindle, 6 rpm, 24° C.) in different sampling situations.

FIG. 4 shows the change in residual viscosity as a function of time, for samples 1A, 1C, 1D and 1E. It appears that the measured viscosity remains constant, only in case 1D where viscosity matches the expected value exactly.

The residual viscosity is the ratio of viscosity measured over time/viscosity at $t_0$ (obtained just after de-pressurisation and therefore corresponding to the viscosity of the polymer before any possible degradation given the preparation method), multiplied by 100.

Example 2

Sampling at Injection on Land

A viscous polymer solution is prepared by dissolving a powder made of 70 mol % acrylamide and 30 mol % acrylic acid copolymer, partially neutralised using caustic soda. The average mass molecular weight of the copolymer is 18 million. The commercial name for this powder is Flopaam 3630S at SNF.

The water used comes from a water treatment unit in which traces of oxygen are eliminated by adding a 30 ppm ammonium bisulphite solution.

The brine water used is composed as described below (cf. Table 3) and contains about 100 ppm hydrogen sulphide $H_2S$ and 0 ppb $O_2$.

It is known that such water will not degrade the viscosity of the polymer solution, if and only if the solution remains completely free of oxygen. In fact, reintroducing any oxygen in the presence of $H_2S$ and excess reducing agent will have an immediate effect by degrading the molecular weight of the polymer.

TABLE 3 composition of brine for example 2

| for 1,000 g | |
|---|---|
| NaCl | 3.115 g |
| KCl | 0.054 g |
| $CaCl_2$, $2H_2O$ | 0.096 g |
| $MgCl_2$, $6H_2O$ | 0.093 g |
| $Na_2SO_4$ | 0.237 g |
| $NaHCO_3$ | 1.31 g |

Figure 5:
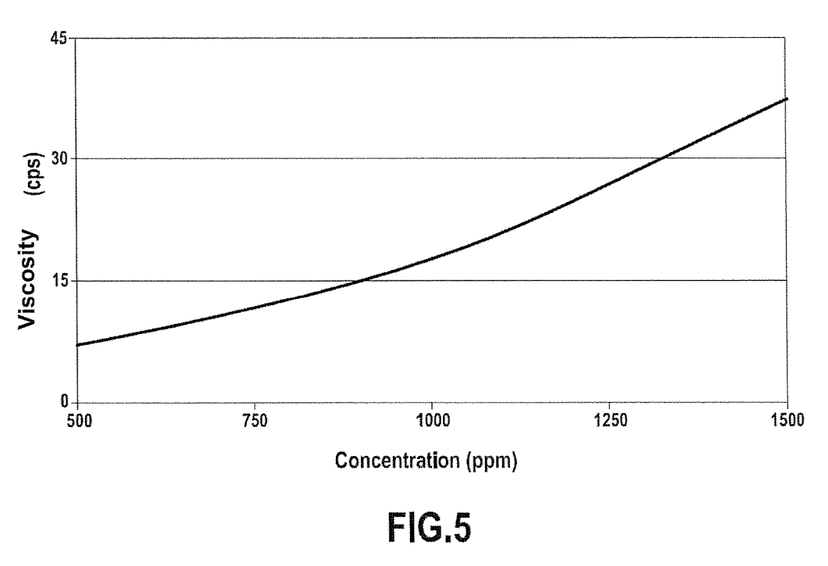
FIG. 5 shows the impact of concentration on the viscosity of a poly(acrylamide-co-acrylic acid) solution measured using a Brookfield viscometer, UL Spindle, 6 rpm, at 46° C.

In order to dissolve the polymer rapidly and avoid contamination with oxygen, the powder is first dissolved using a PSU unit as described in patent application WO2008107492 to obtain a 15,000 ppm polymer solution, then this solution is diluted after two hours maturation time with the same brine water to obtain a polymer solution containing 1,000 ppm polymer, which according to the graph presented in FIG. 5 should generate a viscosity of 18 cps at 46° C. using a Brookfield viscometer with UL module at a speed of 6 rpm.

A sample is collected downstream of the dissolution and dilution unit using a device comprising a sampling cylinder to which is connected a set of non-shearing valves, and a cylinder that may be used to inject a previously-prepared stabilizing solution. The construction of the device is represented schematically in FIG. 2.

The stabilizing solution is a mixture of 10% 1,3,5 triazine, hexahydro-1,3,5-trimethyl 10% diethyl thiourea, 10% HTPO or 4-hydroxy-2,2,6,6-tetramethylpiperidin-1-oxyl, 10% pentaerythritol and water, the percentages being % by weight given for the total weight of the stabilizing solution.

2-A A first sample is collected. The solution sample contained in the sampling cylinder is de-pressurised into a beaker under ambient air and after de-foaming, its viscosity is measured at 35° C. The loss of viscosity is immediate and the value measured in only 5 cps.

2-B A second sample is collected. The cylinder containing the sample collected is then disconnected from the rest of the device, taken to a measuring laboratory, and finally introduced into a glove box, an enclosure rendered inert by nitrogen purging so as to have less than 50 ppb of oxygen in the box in the box. Therefore the measurement is made 6 hours after taking the sample. The viscosity is then 18 cps, which is the expected value. This value therefore confirms that the dissolution line remains strictly anaerobic and that no mechanical degradation occurred. This also confirms the quality of polymer dissolution and the accuracy of its concentration. However, it requires significant and slow measuring resources that do not enable real time or frequent checks of the quality of fluid injected.

2-C A third sample is collected. 100 ppm of stabilizing solution is then added to the sample collected by injection into the sampling cylinder using overpressure. After waiting 10 minutes mixing time, the cylinder is de-pressurised into a beaker under ambient air and after de-foaming the viscosity is measured at 35° C. The viscosity is 9 cps, equivalent to a degradation of about 50% compared to example 2-B, due to inadequate short stopping of the degrading reactions.

2-D A fourth sample is collected. 500 ppm of stabilizing solution is then added to the sample collected by injection into the sampling cylinder using overpressure. After waiting 10 minutes mixing time, the cylinder is de-pressurised into a beaker under ambient air and after de-foaming, the viscosity is measured at 35° C. The viscosity is 18 cps and is the expected value. This value therefore confirms that the dissolution line remains strictly anaerobic and that no mechanical degradation occurred. This also confirms the quality of polymer dissolution and the accuracy of its concentration. This technique requires minor and rapid measuring resources that enable real time and frequent checks of the quality of injected fluid.

Example 3

Sampling at Production on Land

The viscous polymer solution as prepared in example 1 is injected through an injector well into the oil reservoir, which has a permeability of 1.2 D. The distance between the injector well and the producer well where the recovered hydrocarbons exit is such that the polymer takes 200 days to sweep the reservoir. During this propagation, the aqueous solution rises to 46° C. and takes up $H_2S$ to a level of 250 ppb. During this period, the acrylamide groups of the polymer are partially hydrolysed, the polymer concentration falls through adsorption and dilution, and the molecular weight is reduced by chemical degradation. The fluid is then pumped back to the surface using a horse-head type, non-shearing system. The materials of construction lead to the contamination of the fluid with iron at a level of 2 ppm. The reducing nature of the swept rock maintains the oxygen content at zero.

It is known that such water will not degrade the viscosity of the polymer solution, if and only if the solution remains completely free of oxygen. In fact, introducing any oxygen in the presence of $H_2S$ and iron and excess reducing agent will have an immediate effect by degrading the molecular weight of the polymer.

A sample is collected downstream of the pumping unit using a device comprising a sampling cylinder to which is connected a set of non-shearing valves, and a cylinder that may be used to inject a previously-prepared stabilizing solution. The construction of the device is represented schematically in FIG. 2.

The stabilizing solution is a mixture of 10% 1,3,5 triazine, hexahydro-1,3,5-trimethyl 10% diethyl thiourea, 10% HTPO or 4-hydroxy-2,2,6,6-tetramethylpiperidin-1-oxyl, 10% pentaerythritol and water, the percentages being % by weight given for the total weight of the stabilizing solution.

3-A A first sample is collected. The solution contained in the sampling cylinder is de-pressurised into a beaker under ambient air and after defoaming the viscosity is measured at 35° C. The measured viscosity is only 2 cps, corresponding to a polymer concentration of 375 ppm if the molecular weight and anionicity remain identical to those that were injected.

3-B A second sample is collected. The cylinder containing the sample collected is then disconnected from the rest of the device, taken to a measuring laboratory, and finally introduced into a glove box, an enclosure rendered inert by nitrogen purging so as to have less than 50 ppb of oxygen in the box. Therefore the measurement is made 6 hours after collecting the sample. The viscosity is then 14 cps. The sample is then removed from the glove box and measurements of molecular weight, anionicity and polymer concentration were made and the measurements obtained are presented in Table 4 below.

TABLE 4

|  | Injected fluid | Produced fluid |
| --- | --- | --- |
| Anionicity (colloidal titration) | 30 mol % | 43 mol % |
| Molecular weight (IV) | 18 million Daltons | 3 million Daltons |
| Concentration (starch iodine API concentration) | 1,000 ppm | 830 ppm |
| Viscosity (Brookfield) | 18 cps at 46° C. | 14 cps at 35° C. in BAG |

There is an apparent inconsistency between viscosity measured in a glove box and the measured molecular weight. Remeasuring the viscosity of the aqueous solution shows that rapid degradation took place when the solution was exposed to the air, viscosity falling to 3.5 cps. The molecular weight measurement is therefore incorrect and no conclusion can be drawn about the mobility ratio between the oil phase and the aqueous phase dilution phase actually established when sweeping the reservoir.

3-C A third sample is collected. 500 ppm of stabilizing solution is then added to the sample collected by injection into the sampling cylinder using overpressure. After waiting 10 minutes mixing time, the cylinder is de-pressurised into a beaker under ambient air and after de-foaming, the viscosity is measured at 35° C. The viscosity is 14 cps, consistent with the value in 3-B. The sample is then subject to measurements of molecular weight, anionicity and polymer concentration and the measurements obtained are presented in Table 5 below.

TABLE 5

|  | Injected fluid | Produced fluid |
| --- | --- | --- |
| Anionicity | 30 mol % | 43 mol % |
| Molecular weight | 18 million Daltons | 13 million Daltons |
| Concentration | 1,000 ppm | 830 ppm |
| Viscosity | 18 cps at 46° C. | 14 cps at 35° C. |

The molecular weight and viscosity are entirely consistent and enable easy and rapid checks to be made of the fluid viscosity that has swept the reserve and thus to correlate data for the increase in oil recovery with the actual mobility value, to monitor polymer breakthrough, to prevent uncontrolled degradation of the polymer and therefore, if necessary, to decide the injection of stabilisers.

The invention claimed is:

1. A sampling procedure for an aqueous hydrosoluble polymer solution flowing in a main circuit, enabling a sample to be collected to undergo at least one characterisation under ambient air comprising:
    obtaining the sample by adding to the aqueous hydrosoluble polymer solution a stabilizing solution, according to a discontinuous addition method:
    the discontinuous addition method comprising:
    adding the stabilizing solution, either after sampling, or, before sampling, to the aqueous hydrosoluble polymer solution circulating in the main circuit, and
    obtaining a sample comprising a mixture of aqueous hydrosoluble polymer solution and stabilizing solution, wherein the aqueous hydrosoluble polymer is protected against attacks it may undergo, in the absence of a stabilizing solution, in an atmosphere containing at least 10% by volume of oxygen;
    wherein the stabilized solution is added in a predetermined quantity, based on a viscosity of the sample and over a predetermined time based on a flow rate of the aqueous polymer solution circulating in the main circuit, to the collected sample so that the sample contains a mixture of the stabilizing solution and the aqueous hydrosoluble polymer solution.

2. Sampling procedure according to claim 1 characterised in that the at least one characterization under ambient temperature is the measurement of viscosity and the added stabilizing solution enables the measured viscosity of the sample to be maintained approximately constant, when said viscosity is measured in ambient air, for a period of at least 1 hour.

3. Sampling procedure according to claim 1 characterised in that the sampling procedure comprises a prior determining of the volume of stabilizing solution to be added to the aqueous hydrosoluble polymer solution in which the volume of stabilizing solution added is varied and the change in measured viscosity of the mixtures obtained is studied over time.

4. Sampling procedure according to claim 1 characterised in that the sampling procedure comprises an analysis step under ambient air for the sample comprising a mixture of the aqueous hydrosoluble polymer solution and the stabilizing solution.

5. Sampling procedure according to claim 1 characterised in that the volume of stabilizing solution in the sample is less than 25% of the total sample volume.

6. Sampling procedure according to claim 1 characterised in that the stabilizing solution contains at least one stabilizing agent chosen from deoxygenating agents, precipitating agents, free radical scavengers, complexing agents, $H_2S$-absorbing agents and sacrificial agents.

7. Sampling procedure according to claim 1 characterised in that the stabilizing solution contains at least three stabilizing agents chosen from deoxygenating agents, precipitating agents, free radical scavengers, complexing agents, $H_2S$-absorbing agents and sacrificial agents.

8. Sampling procedure according to claim 1 characterised in that the aqueous hydrosoluble polymer solution circulates in a main circuit (II) used in enhanced oil recovery, the aqueous hydrosoluble polymer solution either on the injection side or on the production side and the sample is collected downstream and/or upstream of the oil reservoir.

9. Sampling procedure according to claim 1 characterised in that the sampling procedure includes a sampling step from a volume of aqueous hydrosoluble polymer solution in a sampling tank (1) using a sampling pipe (3) fitted with a non-shearing sampling closure (6) and a step adding into the sampling tank (1) a volume of stabilizing solution (300), sampling steps being carried out under hermetically-sealed conditions.

10. Sampling procedure according to claim 1 characterised in that the sampling procedure includes providing a sampling device connected to the main circuit (II) in which the aqueous hydrosoluble polymer solution (200) to be sampled in circulating, comprising:
    a first vessel (1), called the sampling tank, capable of containing the sample (100) collected, including:
        an inlet (5) for aqueous polymer solution to be sampled, and a sampling pipe (3) connecting the inlet (5) to the main circuit (II), the said sampling pipe (3) being fitted with a non-shearing sampling closure (6) and capable of being connected to the main circuit (II) and
        an outlet (8) and outlet pipe (7) fitted with an outlet closure (9) and connected to the outlet (8),
    a second vessel (2), called the treatment tank, capable of containing a stabilizing solution (300), comprising an outlet (10) for the stabilizing solution (300), a connecting pipe (4) connected to the outlet (10) for the stabilizing solution and fitted with a treatment closure (11) and, the connecting pipe (4) providing, at least in part, the connection between the treatment tank (2) and the sampling tank (1),
and where the sampling tank (1) is connected hermetically to the main pipe, and is isolated hermetically when the sampling closure (6), outlet closure (9) and treatment closure (11).

* * * * *